United States Patent [19]

Asato et al.

[11] Patent Number: 4,886,784

[45] Date of Patent: Dec. 12, 1989

[54] NOVEL 23-IMINO DERIVATIVES OF 23-KETO COMPOUNDS

[75] Inventors: Goro Asato, Titusville; Donald J. France, Pennington, both of N.J.

[73] Assignee: American Cyanamid Company, Stamford, Conn.

[21] Appl. No.: 88,954

[22] Filed: Aug. 27, 1987

Related U.S. Application Data

[63] Continuation-in-part of Ser. No. 907,188, Sep. 12, 1986, Pat. No. 4,849,446.

[51] Int. Cl.$^4$ .................... A61K 31/365; C07D 493/22
[52] U.S. Cl. ...................................... 514/30; 536/7.1; 549/264
[58] Field of Search .................... 549/264; 536/7.1; 514/450, 30

[56] References Cited

U.S. PATENT DOCUMENTS

| | | | |
|---|---|---|---|
| 4,289,760 | 9/1981 | Mrozik et al. | 549/264 |
| 4,457,920 | 7/1984 | Mrozik | 549/264 |
| 4,547,520 | 10/1985 | Ide et al. | 549/264 |

Primary Examiner—Richard L. Raymond
Assistant Examiner—Mark W. Russell
Attorney, Agent, or Firm—Estelle J. Tsevods

[57] ABSTRACT

The present invention relates to novel 23-imino derivatives of the compounds collectively referred to as 23-keto C-076 compounds. The C-076 compounds (collectively) are isolates from the fermentation broth of *Streptomyces avermitilis*. These novel compounds have potent anthelmintic, insecticidal, ectoparasiticidal, nematicidal and acaricidal activity. Compositions containing these 23-imino derivatives of 23-keto C-076 also are described herein.

8 Claims, No Drawings

NOVEL 23-IMINO DERIVATIVES OF 23-KETO COMPOUNDS

This application is a continuation-in-part of copending application Ser. No. 907,188, filed Sept. 12, 1986, now U.S. Pat. No. 4,849,446.

BACKGROUND OF THE INVENTION

The present invention relates to new 23-imino derivatives of the compounds collectively defined as 23-keto C-076 compounds. These C-076 antibiotics preferably are produced by the fermentation of the microorganism *Streptomyces avermitilis*. The morphological characteristics, compounds and method for the production of the 23-keto C-076 compounds is disclosed in U.S. Pat. No. 4,289,760, issued to Mrozik et al on Sept. 15, 1981 and in German Patent Publication No. P 2717040.7-42 both incorporated herein by reference.

The C-076 compounds are complex macrolides which have a 23-hydroxy substituent, as well as two other hydroxy groups. The selective oxidation of this 23-hydroxy group to a 23-oxo group is disclosed. The present invention provides a further derivatization of the oxo group to afford 23-imino derivatives. These 23-imino derivatives of the C-076 compounds are useful for the prevention, treatment or control of helmintic, ectoparasitic, insect, acarid and nematode infections and infestations in warm-blooded animals and agricultural crops.

SUMMARY OF THE INVENTION

The present invention provides novel 23-imino derivatives of the compounds designated 23-keto (or oxo) C-076 compounds.

The 23-keto C-076 compounds have the following structural formula:

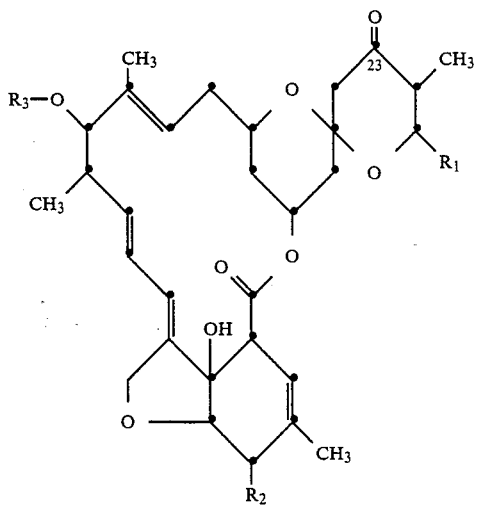

wherein, $R_1$ is isopropyl or sec-butyl;

$R_2$ is methoxy, hydroxy, lower alkanoyloxy or substituted lower alkanoyloxy wherein the substituent is hydroxy, carboxy, phenoxy or mono-, di- or trihalo such as trifluoroacetyl, trichloroacetyl, chloroacetyl and the like; and $R_3$ is hydrogen, α-L-oleandrosyl, 4'-(α-L-oleandrosyl)-α-L-oleandrosyl, 4"-lower alkanoyl-4'-(α-L-oleandrosyl)-α-L-oleandrosyl, or 4"(substituted lower alkanoyl)-4'-(α-L-oleandrosyl)-α-L-oleandrosyl wherein the substituent is hydroxy, carboxy, phenoxy or mono-, di, or tri-halo such as trifluoroacetyl, trichloroacetyl, chloroacetyl and the like.

The compounds of the present invention are useful anthelmintics, ectoparasiticides, insecticides, acaricides and nematicides in treating, preventing or controlling such diseases in warm-blooded animals, such as poultry, cattle, sheep, swine, rabbits, horses, dogs, cats and human beings and agricultural crops.

Although these diseases have been recognized for years and therapies exist for the treatment and prevention of the diseases, the present invention provides novel compounds in the search for effective such therapy. For instance, U.S. application for Letters Pat. Ser. Nos. 907,186, 907,187, 907,259, 907,281, 907,283 and 907,284 of Asato and Asato et al, filed September 12, 1986 and incorporated herein by reference thereto provide compounds for such treatments. European Patent Application Publication No. 170,006 also provides such compounds.

U.S. Pat. No. 3,950,360, Aoki et al, April 13, 1976 discloses certain antibiotic substances obtained by culturing a Streptomyces microorganism, said compounds being useful as insecticides and acaricides. Further, an entire series of U.S. patents relates to certain compounds produced by the fermentation of *Streptomyces avermitilis* (U.S. Pat. No. 4,171,314, Chabala et al, Oct. 16, 1979; U.S. Pat. No. 4,199,569, Chabala et al, Apr. 22, 1980; U.S. Pat. No. 4,206,205, Mrozik et al, June 3, 1980; U.S. Pat. No. 4,310,519, Albers-Schonberg, Jan. 12, 1982; U.S. Pat. No. 4,333,925, Buhs et al, June 8, 1982). U.S. Pat. No. 4,423,209, Mrozik, Dec. 27, 1983 relates to the process of converting some of these less desirable components to more preferred ones. Finally, British Patent Application No. 2166436 A discloses antibiotics also.

The present compounds or the pharmaceutically and pharmacologically acceptable salts thereof exhibit excellent and effective treatment, prevention and/or control of these serious diseases of warm-blooded animals.

It is an object of the present invention, therefore, to provide novel 23-imino derivatives of 23-keto C-076 compounds. It is a further object to provide a process for the preparation of these derivatives and to provide methods for preventing, treating or controlling endo and ectoparasitic (collectively parasitic), insect, nematode, acarid and helmintic diseases in warm-blooded animals and agricultural crops by providing compositions containing prophylactically, therapeutically or pharmaceutically-effective amounts of the present novel compounds.

These and other objects of the invention will become apparent by the more detailed description of the invention provided hereinbelow.

DETAILED DESCRIPTION OF THE INVENTION

The 23-keto C-076 compounds which may act as precursors of the present compounds are represented by the following structural formula, wherein, $R_1$ is isopropyl or sec-butyl;

$R_2$ is methoxy, hydroxy, lower alkanoyloxy or substituted lower alkanoyloxy wherein the substituent is hydroxy, carboxy, phenoxy or mono-, di- or tri-halo such as trifluoroacetyl, trichloroacetyl, chloroacetyl and the like; and $R_3$ is hydrogen, α-L-oleandrosyl, 4'-(α-L-oleandrosyl)-α-L-oleandrosyl, 4''-lower alkanoyl-4'-(α-L-oleandrosyl)-α-L-oleandrosyl, or 4''(substituted lower alkanoyl)-4'-(α-L-oleandrosyl)-α-L-oleandrosyl wherein the substituent is hydroxy, carboxy, phenoxy or mono-, di, or tri-halo such as trifluoroacetyl, trichloroacetyl, chloroacetyl and the like.

The compounds of the instant invention are represented by the following structural formula:

wherein, $R_1$ is 4'-(α-L-oleandrosyl)-α-L-oleandrosyl or α-L-oleandrosyl; $R_2$ is isopropyl or sec-butyl; $R_3$ is methoxy, hydroxy, acetoxy, methoxyacetoxy or chloroacetoxy; X is $NOR_4$, or $N—NHR_5$; $R_4$ is hydrogen, $C_1$–$C_6$ alkyl, $C_1$–$C_4$ alkoxymethyl, benzyl, allyl, propargyl, phenyl, $CH_2COO$-alkyl ($C_1$–$C_4$), N-($C_1$–$C_6$ alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1$–$C_6$ alkanoyl, chloroacetyl, methoxyacetyl, phenylacetyl optionally substituted on the phenyl ring with one or two halogens, $C_1$–$C_4$ alkyl groups, $C_1$–$C_4$ alkoxy groups, or nitro groups, phenoxyacetyl optionally substituted on the phenyl ring by one or two halogens, $C_1$–$C_4$ alkyl groups, $C_1$–$C_4$ alkoxy groups, or nitro groups, or benzoyl optionally substituted with one or two halogens, $C_1$–$C_4$ alkyl groups, $C_1$–$C_4$ alkoxy groups, or nitro groups; $R_5$ is $$\overset{O}{\underset{}{\|}}{C-NR_6R_7}, \overset{S}{\underset{}{\|}}{C-NR_6R_7}, \overset{O}{\underset{}{\|}}{C-OR_6}, \overset{\overset{O}{\|}}{\underset{}{\|}}{CCNR_6R_7}, \overset{O}{\underset{\underset{O}{\|}}{\|}}{SR_9},$$

$C_1$–$C_6$ alkanoyl, formyl, $C_1$–$C_6$ alkyl, $$\overset{NH}{\underset{}{\|}}{C-NR_6R_7},$$

benzoyl optionally substituted with one or two halogens, $C_1$–$C_4$ alkyl groups, $C_1$–$C_4$ alkoxy groups, or nitro groups; $R_6$ and $R_7$ are hydrogen, $C_1$–$C_6$ alkyl, or phenyl optionally substituted with one or two halogens, $C_1$–$C_4$ alkyl groups, $C_1$–$C_4$ alkoxy groups, or nitro groups; $R_8$ is $C_1$–$C_6$ alkyl or phenyl optionally substituted with one or two halogens, $C_1$–$C_4$ alkyl groups, $C_1$–$C_4$ alkoxy groups, or nitro groups; $R_9$ is $C_1$–$C_6$ alkyl or phenyl optionally substituted with one or two halogens, $C_1$–$C_4$ alkyl groups, $C_1$–$C_4$ alkoxy groups, or nitro groups; and the pharmaceutically and pharmacologically acceptable salts thereof.

A preferred group of compounds of structure (I) is defined by

X, $R_1$, $R_2$, $R_4$, $R_5$, $R_6$, $R_7$, $R_8$ and $R_9$ as defined hereinabove; and $R_3$ as hydroxy or methoxy.

Another preferred group of compounds of structure (I) is defined by

X is $NOR_4$ or $N—NHR_5$, wherein $R_4$ is $C_1$–$C_3$ alkyl, CONH-alkyl($C_1$–$C_2$), $CONHC_6H_5$, CONH-4-chlorophenyl, CONH-3,4-dichlorophenyl or $CONHCH_2C_6H_5$;

$R_5$ is $$\overset{O}{\underset{}{\|}}{C-NR_6R_7}, \overset{O}{\underset{}{\|}}{C-OR_8}$$

or $C_1$–$C_6$ alkyl;

$R_2$ is isopropyl or sec-butyl;

$R_3$ is hydroxy; and $R_1$, $R_6$, $R_7$ and $R_8$ are as defined hereinabove.

The most preferred group of compounds of structure (I) is where

X is $NOR_4$ or $N—NHR_5$ $R_1$ is 4'-(α-L-oleandrosyl)-α-L-oleandrosyl.

$R_2$ is isopropyl or sec-butyl;

$R_3$ is hydroxy;

$R_4$ is $C_1$–$C_6$ alkyl; and $R_5$ is

The imino derivatives of the 23-keto (oxo) compounds are readily prepared by standard techniques such as procedures described by S. M. McElvain in *The Characterization of Organic Compounds*, published by MacMillan Company, New York, 1953, pages 204–205 and incorporated herein by reference.

Typically, a 23-oxo compound is stirred in alcohol, such as methanol or ethanol, or dioxane in the presence of acetic acid and an excess of the amino derivatizing agent, such as hydroxylamine hydrochloride, methoxyamine hydrochloride, semicarbazide hydrochloride and the like along with an equivalent amount of sodium acetate, at room temperature (25° C.) to 50° C. The reaction is usually complete in several hours to several days at room temperature but can be readily speeded by heating.

The compounds of structure (I) wherein X is $NOR_4$ and $R_4$ is $C_1$–$C_6$ alkoxycarbonyl, chloroacety, methoxyacety, phenylacety, $C_1$–$C_6$ alkyl-NHCO, are prepared by treating the structure (I) compounds, wherein X is NOH, with acid anhydrides or isocyanates. The reactions are conducted in inert solvents, such as methylene chloride, ethylene dichloride or dioxane, in the presence of a tertiary amine such as triethylamine or diisopropylethylamine. Generally, the reactions are conducted from 0° C. to room temperature (25° C.), but if the reactions are sluggish, heat is applied. An equivalent to a slight excess of the acid anhydride is used to avoid reaction at the 5- or 4"-hydroxy groups.

The novel compounds of the present invention have significant activity as anthelmintics, ectoparasiticides, insecticides, nematicides and acaricides in human and animal health areas and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oestophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Paracaris. Certian of these, such as Nematodirus, Cooperia, and Oesphagostomum primarily attack the intestinal tract while others, such as Haemonchus and Ostertagia, are most prevalent in the stomach. Still others such as Dictyocaulus are found in the lungs. Also, other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs, and if left untreated, may result in death of the infected host. The 23-imino derivatives of the 23-keto C-076 compounds of this invention unexpectedly have high activity against these parasites. Additionally, they also are active against Dirofilaria in dogs, Nematospiroides, Syphacia, Aspiculuris in rodents, arthropod ectoparasites such as ticks, mites, lice, fleas, blowfly of animals and birds, the ectoparasite Lucilia sp. of sheep, biting insects and migrating dipterous larvae such as Hypoderma sp. in cattle, Gastrophilus in horses and Cuterebra sp. in rodents.

The compounds of the present invention also are useful in treating, preventing or controlling parasites which infect human beings, as well. The most common genera of parasites of the gastrointestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra-intestinal stages of the intestinal worms Strongyloides and Trichinella. The present compounds also are of value against arthropods parasitizing man, biting insects and other dipterous pests causing annoyance to man.

These compounds further are active against household pests such as the cockroach, Blattella sp., clothes moth, Tineola sp., carpet beetle, Attagenus sp., and the housefly *Musca domestica*.

Insect pests of stored grains such as Tribolium sp., Tenebrio sp., and of agricultural plants such as spider mites (Tetranycus sp.), southern army worms, tobacco budworms, boll weevils, aphids (Acyrthiosiphon sp.), migratory orthopterans such as locusts and immature stages of insects living on plant tissue are controlled by the present compounds as well as the control of soil nematodes and plant parasites such as Meloidogyne sp., which may be of importance in agriculture.

The compounds of the present invention may be administered orally or parenterally for animal and human usage, while they may be formulated in liquid or solid form for agricultural use. Oral administration may take the form of a unit dosage form such as a capsule, bolus or tablet, or as a liquid drench where used as an anthelmintic for animals.

The animal drench is normally a solution, suspension or dispersion of the active compound, usually in water, together with a suspending agent such as bentonite and a wetting agent or like excipient. Generally, the drenches also contain an antifoaming agent. Drench formulations generally contain about 0.001% to 0.5%, by weight, of the active compound. Preferred drench formulations contain about 0.01% to 0.1% by weight.

Capsules and boluses comprise the active ingredient admixed with a carrier vehicle such as starch, talc, magnesium stearate or di-calcium phosphate.

Where it is desired to administer the 23-imino derivatives of C-076 in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the active compound depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the active compounds of the present invention may be administered to animals parenterally, such as by intraruminal, intramuscular, intratracheal, or subcutaneous injection. In such an event, the active compound is dissolved or dispersed in a liquid carrier vehicle.

For parenteral administration, the active compound is suitably admixed with an acceptable vehicle, preferably of the vegetable oil variety such as peanut oil, cotton seed oil and the like. Other parenteral vehicles such as organic preparations using solketal, propylene glycol, glycerol formal, and aqueous parenteral formulation also are used. The active 23-imino compound or compounds of the present invention are dissolved or suspended in the parenteral formulation for administration. Such formulations generally contain about 0.005% to 5%, by weight, of the active compound.

Although the compounds of the present invention are primarily uses in the treatment, prevention or control of helminthiasis, they also are useful in the prevention and treatment of diseases caused by other parasites. For example, arthropod parasites such as ticks, lice, fleas, mites and other biting insects in domesticated animals and poultry are controlled by the present compounds. These compounds also are effective in treatment of parasitic diseases that occur in other animals including human beings. The optimum amount to be employed will, of course, depend upon the particular compound employed, the species of animal to be treated and the type and severity of parasitic infection or infestation. Generally, the amount useful in oral administration of these novel compounds is about 0.001 mg to 10 mg per kg of animal body weight, such total dose being given at one time or in divided doses over a relatively short period of time (1–5 days). The preferred compounds of the invention give excellent control of such parasites in animals by administering about 0.025 mg to 3 mg per kg of animal body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the animal's feed, or dissolved or suspended in the drinking water, compositions are provided in which the active compound or compounds are intimately dispersed in an inert carrier or diluent. An inert carrier is one that will not react with the active component and that will be administered safely to animals. Preferably, a carrier for feed administration is one that is, or may be, an ingredient of the animal ration.

Suitable compositions include feed premixes or supplements in which the active compound is present in relatively large amounts, wherein said feed premixes or supplements are suitable for direct feeding to the animal or for addition to the feed either directly or after an intermediate dilution or blending step.

Typical carriers or diluents suitable for such compositions include distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing about 0.005% to 2.0%, by weight, of the active compound are particularly suitable as feed premixes.

Feed supplements, which are fed directly to the animal, contain about 0.0002% to 0.3%, by weight, of the active compounds. Such supplements are added to the animal feed in an amount to give the finished feed the concentration of active compound desired for the treatment, prevention and/or control of parasitic diseases. Although the desired concentration of active compound will vary depending upon the factors previously mentioned as well as upon the particular derivative employed, the compounds of this invention are usually fed at concentrations of about 0.00001% to 0.02% in the feed in order to achieve the desired antiparasitic result.

The compounds also may be administered by pouring on the skin of animals via a solution. Generally, the active compounds are dissolved in a suitable inert solvent, such as dimethylsulfoxide, propylene glycol of the like, alternatively in combination of solvents, for the pour-on administration.

The compounds of this invention also are useful in combating agricultural pests that inflict damage upon growing or stored crops. The present compounds are applied, using known techniques such as sprays, dusts, emulsions and the like, to the growing or stored crops to effect protection from such agricultural pests.

The present invention is illustrated by the following examples which are illustrated of said invention and not limitative thereof.

EXAMPLES 1 AND 2

23-Methoxime-C-076-B2a

In 54 mL of dry dioxane, 89 mg of 23-keto-C-076-B2a is stirred with 64 mg of MeONH$_2$.HCl, 63 mg of NaOAc and 11 mL of HOAc for 24 hours. The mixture is poured into 200 mL each of CH$_2$Cl$_2$ and H$_2$O, and the layers are separated. The aqueous layer is further extracted with 50 mL of CH$_2$Cl$_2$, and the combined CH$_2$Cl$_2$ extracts are washed with H$_2$O, dried (Na$_2$SO$_4$) and evaporated to dryness. The crude product is purified by preparative layer chromatography (silica gel) using 5% MeOH in CH$_2$Cl$_2$ to afford the title compound, that is identified by mass spectrometry and NMR spectroscopy.

The 23-methoxime-C-076-B2b is prepared similarly.

EXAMPLES 3–15

In the manner described in Examples 1 and 2, the following compounds are prepared by substituting the appropriate O-substituted hydroxylamine hydrochloride for MeONH$_2$.HCl, as needed, and purifying the products by chromatograph on silica gel. The products are identified by mass spectroscopy and NMR spectroscopy.

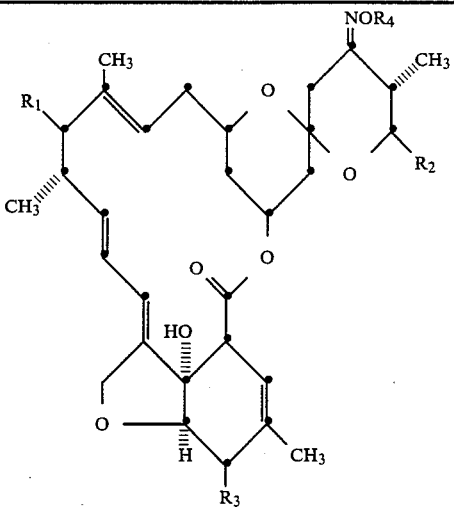

$R_1 = 4'-(\alpha\text{-L-oleandrosyl})-\alpha\text{-L-oleandrosyloxy}$.

| $R_4$ | $R_2$ | $R_3$ |
|---|---|---|
| $C_2H_5OCOCH_2$ | sec-butyl | OH |
| $C_2H_5$ | sec-butyl | OH |
| H | sec-butyl | OH |
| n-$C_3H_7$ | sec-butyl | OH |
| i-$C_3H_7$ | sec-butyl | OH |
| n-$C_6H_{13}$ | sec-butyl | OH |
| Propargyl- | sec-butyl | OH |
| Allyl- | sec-butyl | OH |
| Benzyl- | sec-butyl | OH |
| $C_2H_5$ | i-propyl | $OCH_3$ |
| $C_2H_5$ | sec-butyl | $OCH_3$ |
| Phenyl- | sec-butyl | OH |
| H | i-propyl | OH |

EXAMPLE 16

4″, 5-Di-O-(t-Butyldimethylsilyl)-23-oxime-C-076-B2a

In the manner described in Examples 1 and 2, 4″, 5-di-O-(t-butyldimethylsilyl)-23-keto-C-076-B2a is treated with $NH_2OH\cdot HCl$ to afford the title product. Purification is completed by chromatography on silica gel, and the title compound is characterized by mass spectrometry and NMR spectroscopy.

EXAMPLE 17

23-[O-(Methylcarbamoyl)oxime]-C-076-B2a

In 5 mL of $Et_2O$, 35 mg of 4″, 5-di-O-(t-butyldimethylsilyl)-23-oxime-C-076-B2a is stirred under $N_2$ with 10 μl of $Et_3N$ and 50 μL of methyl isocyanate for 24 hours at room temperature. The ether is evaporated, and the residue is purified on a preparative chromatograpic plate (silica gel) using 5% MeOH in $CH_2Cl_2$. The product is then dissolved in 2 mL of MeOH containing p-toluenesulfonic acid.$H_2O$ (2 mole equivalents) and stirred for 0.5 hours. Then, EtOAc is added, and the solution is washed with $NaHCO_3$ solution and $H_2O$ (3×2 ml) and dried ($Na_2SO_4$). Removal of solvents affords the title compound that is identified by mass spectrometry and NMR spectroscopy.

EXAMPLE 18

4″, 5-Di-O-(t-Butyldimethylsilyl)-23-keto-C-076-B2a

In 5 mL of DMF containing 0.5 g of 23-keto-C-076-B2a, 250 mg of imidazole is added followed by 250 mg of t-butyldimethylsilyl chloride. The reaction mixtures is stirred under $N_2$ for 3 hours at 15° C., and 75 mL of $Et_2O$ and 25 mL of $H_2O$ are added. The layers are separated, and the aqueous layer is extracted further with $Et_2O$. The combined $Et_2O$ layers are washed with $H_2O$ several times, dried ($M_9SO_4$) and evaporated to dryness. The residue is purified by preparative layer chromatography using 5% MeOH in $CH_2Cl_2$. The title compound is identified by mass spectrometry and NMR spectroscopy.

EXAMPLE 19

23-[O-(Acetyl)oxime]-C-076-B2a

In 0.5 mL of pyridine, 25 mg of 4″, 5-di-O(t-butyldimethylsilyl)-23-oxime-C-076-B2a is stirred at 0° C. while 0.05 mL of $Ac_2O$ is added. The mixture is allowed to stir at room temperature for 2 hours and poured into ice-water. The mixture is extracted with $CH_2Cl_2$, and the extract is washed with 5% $NaHCO_3$ solution. After drying ($Na_2SO_4$), the $CH_2Cl_2$ is evaporated to dryness and the residue is dissolved in 2 mL of MeOH and stirred with 20 mg of p-toluenesulfonic acid hydrate at 15° C. for 0.5 hours. The mixture is diluted with 5 mL of $CH_2Cl_2$, and the solution is washed with dilute $NaHCO_3$ solution and water. The solution is dried ($Na_2SO_4$) and chromatographed over silica gel using 2% MeOH in $CH_2Cl_2$ to afford the title compound that is identified by mass spectrometry and NMR spectroscopy.

The title compound also is prepared by dissolving 100 mg of 23-oxime-C-076-B2a in 3 mL of $CH_2Cl_2$ containing 52 mg of diisopropylethylamine and adding 25 mg of acetic anhydride in 0.5 mL of $Ch_2Cl_2$ at 0° C. After an hour, the mixture is quenched with ice, extracted with $CH_2Cl_2$, and the $CH_2Cl_2$ solution is evaporated to dryness. The crude product is then purified by chromatography in the manner described hereinabove to afford the title compound.

EXAMPLE 20–26

23-[O-(substituted)oxime]-C-076-Compounds

In the manners described in Example 19, the following compounds are prepared by using the requisite acid anhydride with appropriate 23-oxime-C-076 compounds

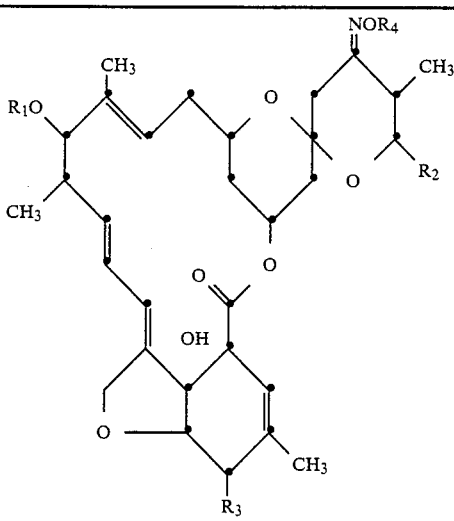

| $R_1$ | $R_2$ | $R_3$ |
|---|---|---|
| ClCH$_2$CO | sec-butyl | OH |
| CH$_3$OH$_2$CO | sec-butyl | OH |
| n-C$_3$H$_7$CO | sec-butyl | OH |
| benzyl-CO | sec-butyl | OH |
| benzoyl- | sec-butyl | OH |
| CH$_3$OCH$_2$CO | i-propyl | OH |
| CH$_3$OCH$_2$CO | sec-butyl | CH$_3$O | and $R_1$ is 4'-(α-L-oleandrosyl)-α-L-oleandrosyl.

EXAMPLES 27–37

23-[O-(N-substituted carbamoyl)oxime]-C-076-B2a (or B2b) Compounds

In the manner described in Example 17, the following 23-O-(N-substituted carbamoyl)oximes of C-076 compounds are prepared by using the appropriate isocyanates and 4″, 5-di-O-(t-butyldimethylsilyl)-23-oxime-C-076-B2a (or B2b) compounds:

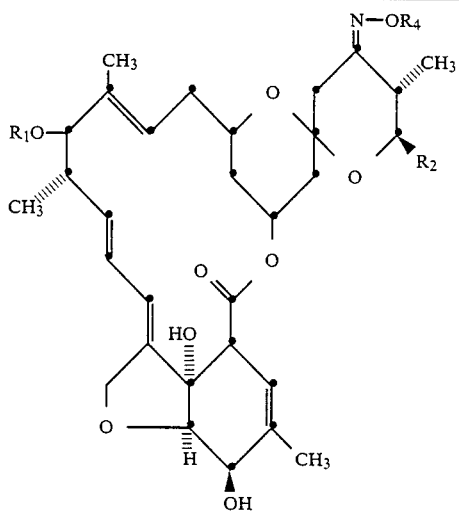

| $R_4$ | $R_2$ |
|---|---|
| C$_2$H$_5$NCO | sec-butyl |
| i-C$_3$H$_7$NHCO | sec-butyl |
| n-C$_6$H$_{13}$NHCO | sec-butyl |
| Benzyl-NHCO | sec-butyl |
| Phenyl-NHCO | sec-butyl |

-continued

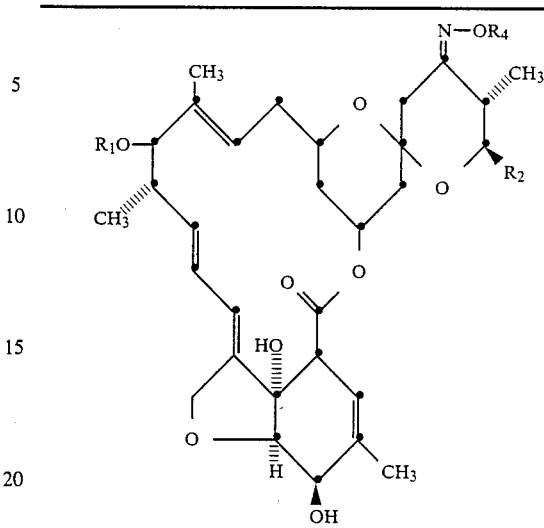

| $R_4$ | $R_2$ |
|---|---|
| 3,4-Dichlorophenyl-NHCO | sec-butyl |
| 4-Chlorophenyl-NHCO | sec-butyl |
| Allyl-NH—CO | sec-butyl |
| Propargyl-NH—CO | sec-butyl |
| C$_2$H$_5$NHCO | i-propyl |
| CH$_3$NHCO | i-propyl | and $R_1$ is 4'-(α-L-oleandrosyl)-α-L-oleandrosyl.

EXAMPLES 38–39

23-Methoxime-C-076-B2a-4″, 5-di-O-Acetate

By the procedure described in Examples 1 and 2, 23-keto-C-076-B2a-4″, 5-di-O-acetate is reacted with MeONH$_2$.HCl to afford the title compound that is purified over silica gel and identified by mass spectrometry and NMR spectroscopy.

Similarly, the 23-methoxime-C-076-B2a-5-O-acetate is prepared in the above manner from its corresponding ketone.

EXAMPLE 40

23-Methoxime-C-076-B2a-4″, 5-di-O-chloroacetate

In the manner described in Examples 1 and 2, 23-keto-C-076-B2a-4″, 5-di-O-chloroacetate is converted into the title compound. This is then purified by chromatography over silica gel and identified by mass spectral analysis and NMR spectroscopy.

EXAMPLES 41–47

23-(2-Carbomethoxyhydrazone)-C-076-B2a

In 15 mL of MeOH, 50 mg of 23-keto-C-076-B2a is stirred with 25 mg of methyl carbazate in the presence of 10 μL of HOAc. After 3 days, the mixture is poured on ice and diluted with H$_2$O. The aqueous phase is saturated with sale, and then is extracted CH$_2$Cl$_2$ several times. The extracts are dried (Na$_2$SO$_4$) and evaporated to dryness. The residue is chromatographed on silica gel using 2% isopropanol in CH$_2$Cl$_2$ as eluent to afford the title compound.

In the same manner, the 2-carbethoxyhydrazone and 2-carbobutoxyhydrazones are prepared using the corresponding carbazates. The 2-carbomethoxyhydrazone and 2-carbethoxyhydrazones of 13-deoxy-23-oxo-C-076-B2a-aglycone are also prepared in the same manner.

Also 1-methylhydrazine and acethydrazide are substituted for methylcarbazate to afford 23-(1-methylhydrazone)-C-076-B2a and 23-(acethydrazone)-C-076-B2a, respectively.

EXAMPLES 48–55

23-Semicarbazide-C-076-B2a

In the manner described in Examples 1 and 2, semicarbazide hydrochloride is substituted for MeONH$_2$.HCl, and the reaction mixture is stirred for 6 days to afford the title compound after purification by chromatography.

Similarly, the semicarbazone and thiosemicarbazone of 13-deoxy-23-oxo-C-076-B2a-aglycone are prepared from the corresponding N-substituted thiosemicarbazides and semicarbazides.

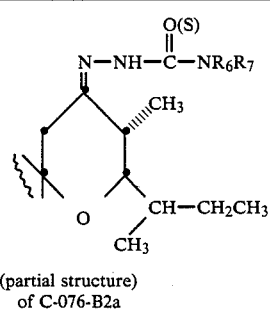

(partial structure) of C-076-B2a

| R$_6$ | R$_7$ |
|---|---|
| CH$_3$ | H |
| CH$_3$ | CH$_3$ |
| n-C$_4$H$_9$ | H |
| CH$_3$ | H (thiosemicarbazone) |
| CH$_3$ | CH$_3$ (thiosemicarbazone) |

EXAMPLES 56–59

Imino Derivatives of 23-Keto-C-076-B2a-Monosaccharide

The following 23-imino derivatives of 23-keto-C-076-B2a-monosaccharide are prepared using the methods in the Examples specified:

| | |
|---|---|
| 23-Methoxime | Examples 1 and 2 |
| 23-Semicarbazone | Examples 48–55 |
| 23-(1-Methylhydrazone) | Examples 41–47 |
| 23-Acethydrazone | Examples 41–47 |

What is claimed is:

1. A compound represented by structural formula (I):

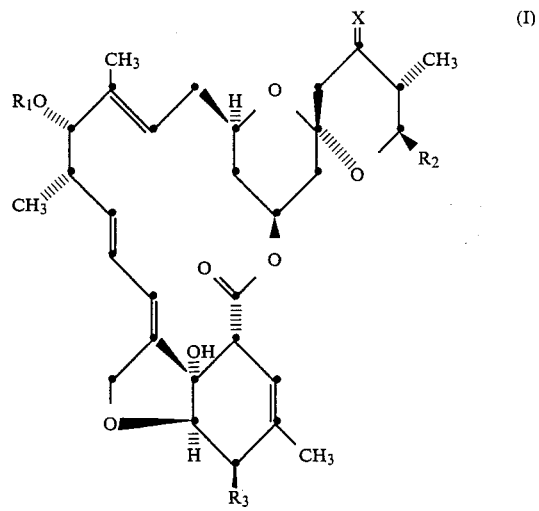

wherein,

R$_1$ is 4'-(α-L-oleandrosyl)-α-L-oleandrosyl or α-L-oleandrosyl;

R$_2$ is isopropyl or sec-butyl; R$_3$ is methoxy, hydroxy, acetoxy, methoxyacetoxy or chloroacetoxy; X is NOR$_4$ or N—NHR$_5$; R$_4$ is C$_1$–C$_4$ alkoxymethyl, CH$_2$COO-alkyl (C$_1$–C$_4$), N-(allyl)-carbamoyl, N-(propargyl)carbamoyl, phenylacetyl substituted on the phenyl ring with one or two halogens, C$_1$–C$_4$ alkyl groups, C$_1$–C$_4$ alkoxy groups or nitro groups, phenoxyacetyl optionally substituted on the phenyl ring by one or two halogens, C$_1$–C$_4$ alkyl groups, C$_1$–C$_4$ alkoxy groups or nitro groups, or benzoyl substituted with one or two halogens, C$_1$–C$_4$ alkyl groups, C$_1$–C$_4$ alkoxy groups or nitro groups; R$_5$ is

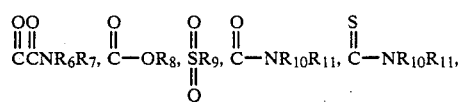

C$_1$–C$_6$ alkanoyl, C$_5$–C$_6$ alkyl,

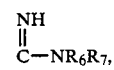

benzoyl optionally substituted with one or two halogens, C$_1$–C$_4$ alkyl groups, C$_1$–C$_4$ alkoxy groups or nitro groups; R$_6$ and R$_7$ are hydrogen, C$_1$–C$_6$ alkyl, or phenyl optionally substituted with one or two halogens, C$_1$–C$_4$ alkyl groups, C$_1$–C$_4$ alkoxy groups or nitro groups; R$_8$ is C$_5$–C$_6$ alkyl or phenyl optionally substituted with one or two halogens, C$_1$–C$_4$ alkyl groups, C$_1$–C$_4$ alkoxy groups or nitro groups; R$_9$ is C$_1$–C$_6$ alkyl or phenyl optionally substituted with one or two halogens, C$_1$–C$_4$ alkyl groups, C$_1$–C$_4$ alkoxy groups or nitro groups; R$_{10}$ and R$_{11}$ are hydrogen, C$_5$–C$_6$ alkyl or phenyl optionally substituted with one or two halogens, C$_1$–C$_4$ alkyl groups, C$_1$–C$_4$ alkoxy groups or nitro groups, with the proviso that both R$_{10}$ and R$_{11}$ are not hydrogen at the same time; or a pharmaceutically and pharmacologically acceptable salt thereof.

2. A compound according to claim 1, wherein $R_3$ is hydroxy or methoxy and X, $R_1$, $R_2$, $R_4$, $R_5$, $R_6$, $R_7$, $R_8$, $R_9$, $R_{10}$ and $R_{11}$ are as described in said claim 1.

3. A compound according to claim 1, wherein X is N—$NHR_5$; $R_5$ is

or $C_5$-$C_6$ alkyl; $R_2$ is isopropyl or sec-butyl; $R_3$ is hydroxy; and $R_1$, $R_8$, $R_{10}$ and $R_{11}$ are as defined in said claim 1.

4. A method for the prevention, treatment or control of endoparasitic or ectoparasitic infections in warm-blooded animals, said method comprising: orally, topically or parenterally administering to an animal infected with endo- or ectoparasites, an endo- or ectoparasiticidally effective amount of a compound represented by structural formula (I),

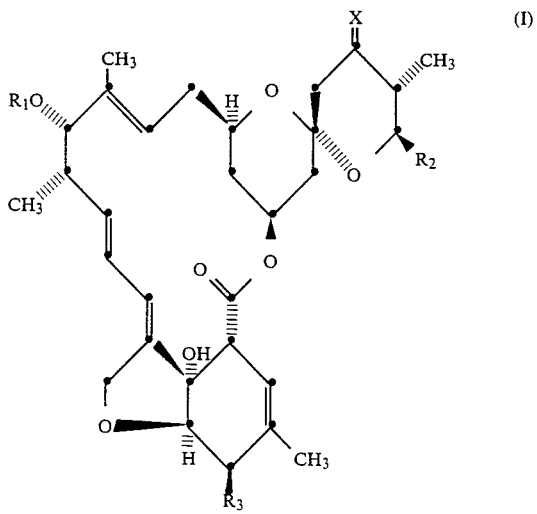

wherein, $R_1$ is 4'-($\alpha$-L-oleandrosyl)-$\alpha$-L-oleandrosyl or $\alpha$-L-oleandrosyl; $R_2$ is isopropyl or sec-butyl; $R_3$ is methoxy, hydroxy, acetoxy, methoxyacetoxy or chloroacetoxy; X is $NOR_4$ or N—$NHR_5$; $R_4$ is $C_1$-$C_4$ alkoxymethyl, $CH_2COO$-alkyl ($C_1$-$C_4$), N-(allyl)-carbamoyl, N-(propargyl)carbamoyl, phenylacetyl substituted on the phenyl ring with one or two halogens, $C_1$-$C_4$ alkyl groups, $C_1$-$C_4$ alkoxy groups or nitro groups, phenoxyacetyl optionally substituted on the phenyl ring by one or two halogens, $C_1$-$C_4$ alkyl groups, $C_1$-$C_4$ alkoxy groups or nitro groups, or benzoyl substituted with one or two halogens, $C_1$-$C_4$ alkyl groups, $C_1$-$C_4$ alkoxy groups or nitro groups; $R_5$ is

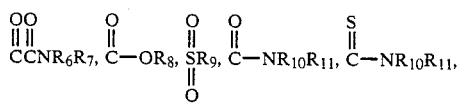

$C_1$-$C_6$ alkanoyl, $C_5$-$C_6$ alkyl,

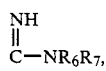

benzoyl optionally substituted with one or two halogens, $C_1$-$C_4$ alkyl groups, $C_1$-$C_4$ alkoxy groups or nitro groups; $R_6$ and $R_7$ are hydrogen, $C_1$-$C_6$ alkyl, or phenyl optionally substituted with one or two halogens, $C_1$-$C_4$ alkyl groups, $C_1$-$C_4$ alkoxy groups or nitro groups; $R_8$ is $C_5$-$C_6$ alkyl or phenyl optionally substituted with one or two halogens, $C_1$-$C_4$ alkyl groups, $C_1$-$C_4$ alkoxy groups or nitro groups; $R_9$ is $C_1$-$C_6$ alkyl or phenyl optionally substituted with one or two halogens, $C_1$-$C_4$ alkyl groups, $C_1$-$C_4$ alkoxy groups or nitro groups; $R_{10}$ and $R_{11}$ are hydrogen, $C_5$-$C_6$ alkyl or phenyl optionally substituted with one or two halogens, $C_1$-$C_6$ alkyl or phenyl optionally substituted with one or two halogens, $C_1$-$C_4$ alkyl groups, $C_1$-$C_4$ alkoxy groups or nitro groups, with the proviso that both $R_{10}$ and $R_{11}$ are not hydrogen at the same time; or a pharmaceutically and pharmacologically acceptable salt thereof.

5. A method for protecting crops, trees, shrubs, stored grain and ornamentals from attack by acarids or insects which infest them, said method comprising: applying an acaricidally or insecticidally-effective amount of a compound represented by structural formula (I),

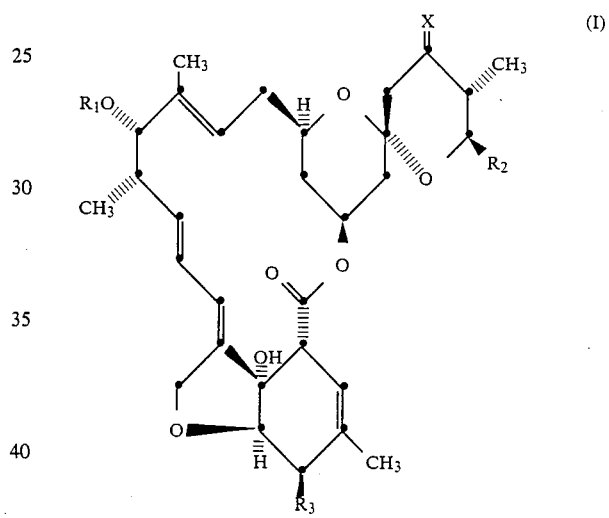

wherein, $R_1$ is 4'-($\alpha$-L-oleandrosyl)-$\alpha$-L-oleandrosyl or $\alpha$-L-oleandrosyl; $R_2$ is isopropyl or sec-butyl; $R_3$ is methoxy, hydroxy, acetoxy, methoxyacetoxy or chloroacetoxy; X is $NOR_4$ or N—$NHR_5$; $R_4$ is $C_1$-$C_4$ alkoxymethyl, $CH_2COO$-alkyl ($C_1$-$C_4$), N-(allyl)-carbamoyl, N-(propargyl)carbamoyl, phenylacetyl substituted on the phenyl ring with one or two halogens, $C_1$-$C_4$ alkyl groups, $C_1$-$C_4$ alkoxy groups or nitro groups, phenoxyacetyl optionally substituted on the phenyl ring by one or two halogens, $C_1$-$C_4$ alkyl groups, $C_1$-$C_4$ alkoxy groups or nitro groups, or benzoyl substituted with one or two halogens, $C_1$-$C_4$ alkyl groups, $C_1$-$C_4$ alkoxy groups or nitro groups; $R_5$ is

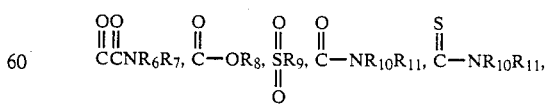

$C_1$-$C_6$ alkanoyl, $C_5$-$C_6$ alkyl,

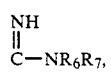

benzoyl optionally substituted with one or two halogens, $C_1-C_4$ alkyl groups, $C_1-C_4$ alkoxy groups or nitro groups; $R_6$ and $R_7$ are hydrogen, $C_1-C_6$ alkyl, or phenyl optionally substituted with one or two halogens, $C_1-C_4$ alkyl groups, $C_1-C_4$ alkoxy groups or nitro groups; $R_8$ is $C_5-C_6$ alkyl or phenyl optionally substituted with one or two halogens, $C_1-C_4$ alkyl groups, $C_1-C_4$ alkoxy groups or nitro groups; $R_9$ is $C_1-C_6$ alkyl or phenyl optionally substituted with one or two halogens, $C_1-C_4$ alkyl groups, $C_1-C_4$ alkoxy groups or nitro groups; $R_{10}$ and $R_{11}$ are hydrogen, $C_5-C_6$ alkyl or phenyl optionally substituted with one or two halogens, $C_1-C_4$ alkyl groups, $C_1-C_4$ alkoxy groups or nitro groups, with the proviso that both $R_{10}$ and $R_{11}$ are not hydrogen at the same time; or a pharmaceutically and pharmacologically acceptable salt thereof.

6. A method for the control of plant nematodes, said method comprising: applying to the foliage of plants, the soil in which they are grown or into the trunks thereof, a nematocidally-effective amount of a compound represented by structural formula (I),

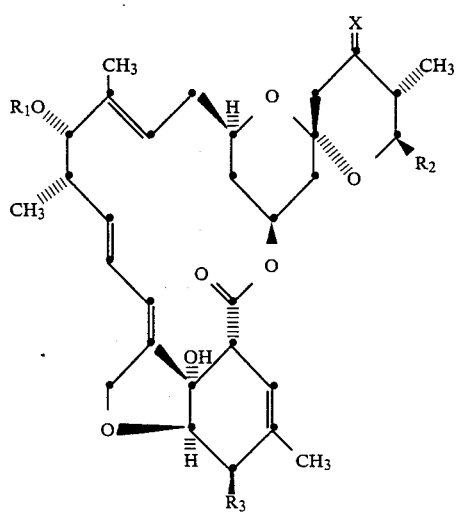

wherein, $R_1$ is 4'-($\alpha$-L-oleandrosyl)-$\alpha$-L-oleandrosyl or $\alpha$-L-oleandrosyl; $R_2$ is isopropyl or sec-butyl; $R_3$ is methoxy, hydroxy, acetoxy, methoxyacetoxy or chloroacetoxy; X is $NOR_4$ or $N-NHR_5$; $R_4$ is $C_1-C_4$ alkoxymethyl, $CH_2COO$-alkyl ($C_1-C_4$), N-(allyl)-carbamoyl, N-(propargyl)carbamoyl, phenylacetyl substituted on the phenyl ring with one or two halogens, $C_1-C_4$ alkyl groups, $C_1-C_4$ alkoxy groups or nitro groups, phenoxyacetyl optionally substituted on the phenyl ring by one or two halogens, $C_1-C_4$ alkyl groups, $C_1-C_4$ alkoxy groups or nitro groups, or benzoyl substituted with one or two halogens, $C_1-C_4$ alkyl groups, $C_1-C_4$ alkoxy groups or nitro groups; $R_5$ is

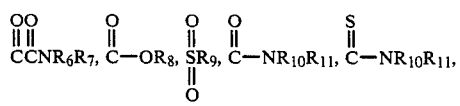

$C_1-C_6$ alkanoyl, $C_5-C_6$ alkyl,

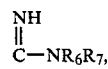

benzoyl optionally substituted with one or two halogens, $C_1-C_4$ alkyl groups, $C_1-C_4$ alkoxy groups or nitro groups; $R_6$ and $R_7$ are hydrogen, $C_1-C_6$ alkyl, or phenyl optionally substituted with one or two halogens, $C_1-C_4$ alkyl groups, $C_1-C_4$ alkoxy groups or nitro groups; $R_8$ is $C_5-C_6$ alkyl or phenyl optionally substituted with one or two halogens, $C_1-C_4$ alkyl groups, $C_1-C_4$ alkoxy groups or nitro groups; $R_9$ is $C_1-C_6$ alkyl or phenyl optionally substituted with one or two halogens, $C_1-C_4$ alkyl groups, $C_1-C_4$ alkoxy groups or nitro groups; $R_{10}$ and $R_{11}$ are hydrogen, $C_5-C_6$ alkyl or phenyl optionally substituted with one or two halogens, $C_1-C_4$ alkyl groups, $C_1-C_4$ alkoxy groups or nitro groups, with the proviso that both $R_{10}$ and $R_{11}$ are not hydrogen at the same time; or a pharmaceutically and pharmacologically acceptable salt thereof.

7. A composition for treating, preventing or controlling endo- or ectoparasitic infections in warm-blooded animals or for controlling insects, said composition comprising: a pharmacologically or insecticidally-effective amount of a compound represented by structural formula (I),

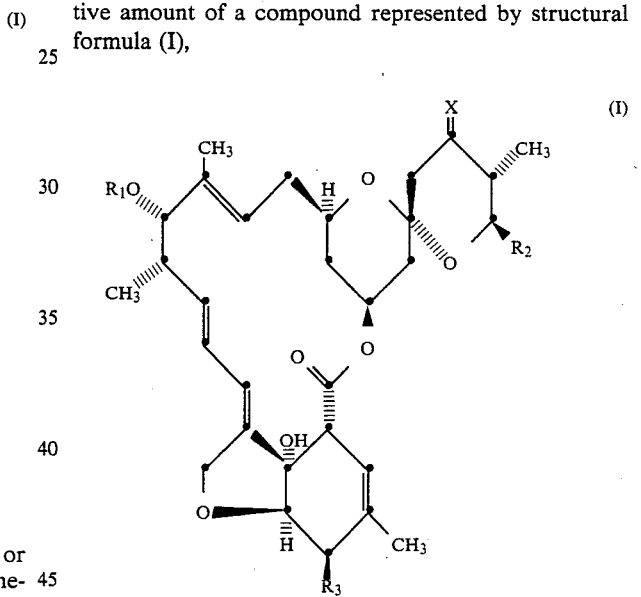

wherein, $R_1$ is 4'-($\alpha$-L-oleandrosyl)-$\alpha$-L-oleandrosyl or $\alpha$-L-oleandrosyl; $R_2$ is isopropyl or sec-butyl; $R_3$ is methoxy, hydroxy, acetoxy, methoxyacetoxy or chloroacetoxy; X is $NOR_4$ or $N-NHR_5$; $R_4$ is $C_1-C_4$ alkoxymethyl, $CH_2COO$-alkyl ($C_1-C_4$), N-(allyl)-carbamoyl, N-(propargyl)carbamoyl, phenylacetyl substituted on the phenyl ring with one or two halogens, $C_1-C_4$ alkyl groups, $C_1-C_4$ alkoxy groups or nitro groups, phenoxyacetyl optionally substituted on the phenyl ring by one or two halogens, $C_1-C_4$ alkyl groups, $C_1-C_4$ alkoxy groups or nitro groups, or benzoyl substituted with one or two halogens, $C_1-C_4$ alkyl groups, $C_1-C_4$ alkoxy groups or nitro groups; $R_5$ is

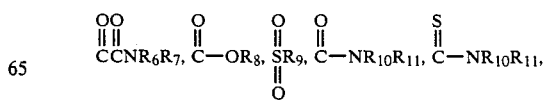

$C_1-C_6$ alkanoyl, $C_5-C_6$ alkyl, $$\overset{NH}{\underset{\|}{C}}-NR_6R_7,$$

benzoyl optionally substituted with one or two halogens, $C_1$-$C_4$ alkyl groups, $C_1$-$C_4$ alkoxy groups or nitro groups; $R_6$ and $R_7$ are hydrogen, $C_1$-$C_6$ alkyl, or phenyl optionally substituted with one or two halogens, $C_1$-$C_4$ alkyl groups, $C_1$-$C_4$ alkoxy groups or nitro groups; $R_8$ is $C_5$-$C_6$ alkyl or phenyl optionally substituted with one or two halogens, $C_1$-$C_4$ alkyl groups, $C_1$-$C_4$ alkoxy groups or nitro groups; $R_9$ is $C_1$-$C_6$ alkyl or phenyl optionally substituted with one or two halogens, $C_1$-$C_4$ alkyl groups, $C_1$-$C_4$ alkoxy groups or nitro groups; $R_{10}$ and $R_{11}$ are hydrogen, $C_5$-$C_6$ alkyl or phenyl optionally substituted with one or two halogens, $C_1$-$C_4$ alkyl groups, $C_1$-$C_4$ alkoxy groups or nitro groups, with the proviso that both $R_{10}$ and $R_{11}$ are not hydrogen at the same time; or a pharmaceutically and pharmacologically acceptable salt thereof; and an inert solid or liquid carrier therefor.

8. A composition according to claim 7 wherein said compound has the structure of formula I; X is N—NHR$_5$; R$_5$ is $$\overset{O}{\underset{\|}{C}}-OR_8, \overset{O}{\underset{\|}{C}}-NR_{10}R_{11}$$

or $C_5$-$C_6$ alkyl; $R_2$ is isopropyl or sec-butyl; $R_3$ is hydroxy; and $R_1$, $R_8$, $R_{10}$ and $R_{11}$ are as defined in said claim 7.

* * * * *

UNITED STATES PATENT AND TRADEMARK OFFICE
CERTIFICATE OF CORRECTION

PATENT NO. : 4,886,784

DATED : December 12, 1989

INVENTOR(S) : Goro Asato; Donald J. France

It is certified that error appears in the above-identified patent and that said Letters Patent is hereby corrected as shown below:

On the cover page, item no. 45, the Date of Patent "Dec." should be replaced with --*Dec.-- and below item no. 73, the following statement should be inserted: --[*] Notice: The portion of the term of this patent subsequent to Jul. 18, 2006 has been disclaimed.--

In claim 4, col. 16, lines 10 and 11, "$C_1$-$C_6$ alkyl or phenyl optionally substituted with one or two halogens," should be deleted.

Signed and Sealed this

Fourth Day of May, 1993

Attest:

MICHAEL K. KIRK

Attesting Officer

Acting Commissioner of Patents and Trademarks